(12) United States Patent
Benson et al.

(10) Patent No.: US 8,503,750 B2
(45) Date of Patent: Aug. 6, 2013

(54) METHOD AND APPARATUS FOR REDUCTION OF METAL ARTIFACTS IN CT IMAGES

(75) Inventors: Thomas Matthew Benson, Clifton Park, NY (US); Naveen Chandra, Kenosha, WI (US); David Allen Langan, Clifton Park, NY (US)

(73) Assignee: General Electric Company, Niskayuna, NY (US)

( * ) Notice: Subject to any disclaimer, the term of this patent is extended or adjusted under 35 U.S.C. 154(b) by 974 days.

(21) Appl. No.: 12/574,502

(22) Filed: Oct. 6, 2009

(65) Prior Publication Data

US 2011/0081071 A1 Apr. 7, 2011

(51) Int. Cl.
*A61B 6/03* (2006.01)
(52) U.S. Cl.
USPC .............................................. 382/131; 378/4
(58) Field of Classification Search
USPC ................... 378/4, 5; 382/128–132
See application file for complete search history.

(56) References Cited

U.S. PATENT DOCUMENTS

| | | | |
|---|---|---|---|
| 4,305,127 A | 12/1981 | Heuscher | |
| 4,590,558 A | 5/1986 | Glover et al. | |
| 5,229,934 A | 7/1993 | Mattson et al. | |
| 5,243,664 A | 9/1993 | Tuy | |
| 6,035,012 A | 3/2000 | Hsieh | |
| 6,101,236 A | 8/2000 | Wang et al. | |
| 6,125,193 A | 9/2000 | Han | |
| 6,266,388 B1 | 7/2001 | Hsieh | |
| 6,721,387 B1 | 4/2004 | Naidu et al. | |
| 7,340,027 B2 | 3/2008 | Timmer | |
| 7,369,695 B2 | 5/2008 | Zettel et al. | |
| 7,539,337 B2 | 5/2009 | Simanovsky et al. | |
| 7,548,604 B2 | 6/2009 | De Man et al. | |
| 2008/0253635 A1 | 10/2008 | Spies et al. | |
| 2009/0074278 A1 | 3/2009 | Beaulieu et al. | |
| 2009/0202036 A1* | 8/2009 | Ziegler et al. | 378/19 |
| 2009/0226060 A1* | 9/2009 | Gering et al. | 382/128 |

OTHER PUBLICATIONS

Mahnken et al., A New Algorithm for Metal Artifact Reduction in Computed Tomography, In Vitro and In Vivo Evaluation After Total Hip Replacement, 2003, Investigative Radiology, vol. 38, No. 12, pp. 769-775.*
Olive et al., Segmentation aided adaptive filtering for metal artifact reduction in radio-therapeutic CT images, 2004, Medical Imaging 2004: Image Processing, SPIE vol. 5370, pp. 1991-2002.*

(Continued)

*Primary Examiner* — Edward Glick
*Assistant Examiner* — John Corbett
(74) *Attorney, Agent, or Firm* — Scott J. Asmus

(57) ABSTRACT

A method and apparatus include acquisition of a view dataset based on x-rays received by a detector corresponding to a energy level, reconstruction of an initial image using the view dataset, the initial image comprising a plurality of metal voxels at respective metal voxel locations, and generation of a metal mask corresponding to the plurality of metal voxels within the initial image. The method and apparatus also include forward projection of the metal mask onto the view dataset to identify metal dexels in the view dataset, performance of a weighted interpolation based on the identified metal dexels to generate a completed view dataset, reconstruction of a final image using the completed view dataset, the final image comprising a plurality of image voxels corresponding to the metal voxel locations, and replacement of a portion of the plurality of image voxels corresponding to the metal voxel locations with smoothed metal values.

26 Claims, 6 Drawing Sheets

OTHER PUBLICATIONS

Oehler et al., The λ-MLEM Algorithm: An Iterative Reconstruction Technique for Metal Artifact Reduction in CT Images, 2007, Springer Proceedings in Physics, vol. 114 Advances in Medical Engineering, ISBN: 978-3-540-68764-1, pp. 42-47.*

Bertram et al., Directional Interpolation of Sparsely Sampled Cone-Beam CT Sinogram Data, 2004, IEEE, pp. 928-931.*

Oehler et al., Evaluation of Surrogate Data Quality in Sinogram-Base CT Metal-Artifact Reduction, Aug. 2008, SPIE vol. 7076, pp. 07-1 to 07-10.*

Takahashi et al., Preliminary Study of Correction of Original Metal Artifacts due to 1-125 Seeds in Postimplant Dosimetry for Prostrate Permanent Implant Brachytherapy, 2006, Radiation Medicine, vol. 24, No. 2, pp. 133-138.*

Siemens AG, Somatom Volume Zoom Computed Tomography System for Volume Scanning, 2001, Order No. A91001-M2110-G138-06-7600, previously available at http://www.whoi.edu/science/B/csi/capabilities/scanner-specs.html.*

De Man et al., "Reduction of Metal Streak Artifacts in X-Ray Computed Tomography Using a Transmission Maximum A Posteriori Algorithm," IEEE Transactions on Nuclear Science, vol. 47, 2000, pp. 977-981.

Glover et al., "Algorithm for the Reduction of Metal Clip Artifacts in CT Reconstructions," Medical Physics, vol. 8, No. 6, Nov./Dec. 1981, pp. 799-807.

Mahnken et al., "A New Algorithm for Metal Artifact Reduction in Computed Tomography," Investigative Radiology, vol. 38, No. 12, Dec. 2003, pp. 769-775.

Kalender et al., "Reduction of CT Artifacts Caused by Metallic Implants," Radiology, vol. 164, No. 2, Aug. 1987, pp. 576-577.

Klotz et al., "Algorithms for the Reduction of CT Artefacts Caused by Metallic Implants," SPIE, vol. 1234, Medical Imaging IV: PACS System Design and Evaluation, 1990, pp. 642-650.

Lewitt et al., "Image Reconstruction From Projections: III: Projection Completion Methods (theory)," Optik, 1978, pp. 189-204.

Lewitt, "Processing of Incomplete Measurement Data in Computed Tomography," Medical Physics, vol. 6, No. 5, Sep./Oct. 1979, pp. 412-471.

Roeske et al., "Reduction of Computed Tomography Metal Artifacts Due to the Fletcher-Suit Applicator in Gynecology Patients Receiving Intercavitary Brachytherapy," American Brachytherapy Society, 2003, pp. 207-214.

Wang et al., "Iterative Deblurring for CT Metal Artifact Reduction," IEEE Transactions on Medical Imaging, vol. 15, No. 5, Oct. 1996, pp. 657-664.

Yu et al., "A Segmentation-Based Method for Metal Artifact Reduction," Academic Radiology, vol. 14, No. 4, Apr. 2007, pp. 495-504.

* cited by examiner

METHOD AND APPARATUS FOR REDUCTION OF METAL ARTIFACTS IN CT IMAGES

BACKGROUND OF THE INVENTION

Embodiments of the invention relate generally to diagnostic imaging and, more particularly, to a method and apparatus for reduction of metal artifacts in CT images.

Typically, in computed tomography (CT) imaging systems, an x-ray source emits a fan or cone-shaped beam toward a subject or object, such as a patient or a piece of luggage. Hereinafter, the terms "subject" and "object" shall include anything capable of being imaged. The beam, after being attenuated by the subject, impinges upon an array of radiation detectors. The intensity of the attenuated beam radiation received at the detector array is typically dependent upon the attenuation of the x-ray beam by the subject. Each detector element of the detector array produces a separate electrical signal indicative of the attenuated beam received by each detector element. The electrical signals are transmitted to a data processing system for analysis which ultimately produces an image.

Generally, the x-ray source and the detector array are rotated about the gantry within an imaging plane and around the subject. X-ray sources typically include x-ray tubes, which emit the x-ray beam at a focal point. X-ray detectors typically include a collimator for collimating x-ray beams received at the detector, a scintillator for converting x-rays to light energy adjacent the collimator, and photodiodes for receiving the light energy from the adjacent scintillator and producing electrical signals therefrom. Typically, each scintillator of a scintillator array converts x-rays to light energy. Each scintillator discharges light energy to a photodiode adjacent thereto. Each photodiode detects the light energy and generates a corresponding electrical signal. The outputs of the photodiodes are then transmitted to the data processing system for image reconstruction.

Generally, in the absence of object scatter, a system derives behavior at a different energy based on a signal from two relative regions of photon energy from the spectrum: the low-energy and the high-energy portions of the incident x-ray spectrum. In a given energy region relevant to medical CT, two physical processes dominate the x-ray attenuation: (1) Compton scatter and the (2) photoelectric effect. The detected signals from two energy regions provide sufficient information to resolve the energy dependence of the material being imaged. Furthermore, detected signals from the two energy regions provide sufficient information to determine the relative composition of an object composed of two hypothetical materials, or the effective atomic number distribution with the scanned object.

Techniques to obtain energy sensitive measurements comprise: (1) scan with two distinctive energy spectra and (2) detect photon energy according to energy deposition in the detector. Such measurements provide energy discrimination and material characterization, and may be used to generate reconstructed images using a base material decomposition (BMD) algorithm. A conventional BMD algorithm is based on the concept that, in an energy region for medical CT, the x-ray attenuation of any given material can be represented by a proper density mix of two materials with distinct x-ray attenuation properties, referred to as the base or basis materials. The BMD algorithm computes two CT images that represent the equivalent density of one of the base materials based on the measured projections at high and low x-ray photon energy spectra, respectively.

A principle objective of energy sensitive scanning is to obtain diagnostic CT images that enhance information (contrast separation, material specificity, etc.) within the image by utilizing two or more scans at different chromatic energy states. A number of techniques have been proposed to achieve energy sensitive scanning including acquiring two or more scans either (1) back-to-back sequentially in time where the scans require multiple rotations of the gantry around the subject or (2) interleaved as a function of the rotation angle requiring one rotation around the subject, in which the tube operates at, for instance, 80 kVp and 140 kVp potentials.

High frequency generators have made it possible to switch the kVp potential of the high frequency electromagnetic energy projection source on alternating views. As a result, data for two or more energy sensitive scans may be obtained in a temporally interleaved fashion rather than two separate scans made several seconds apart as typically occurs with previous CT technology. The interleaved projection data may furthermore be registered so that the same path lengths are defined at each energy using, for example, some form of interpolation.

However, it is known that objects with high x-ray absorption properties (e.g., metal) can cause artifacts in reconstructed CT images, often resulting in images having low- or non-diagnostic image quality. For example, metal implants such as amalgam dental fillings, joint replacements (i.e., plates and/or pins used in hips, knees, shoulders, etc.), surgical clips, or other hardware may generate streak or starburst artifacts in the formation of such images. Such artifacts typically result from the sharp difference in signal attenuation at the boundary of the metal implants and a patient's anatomy.

Many correction techniques or methods are known for reducing or altering such artifact streaks. For example, one known technique for reducing artifact streaks includes the use of iterative image reconstruction algorithms with weighting designed to ameliorate the metal artifacts. However, full iterative reconstruction is not widely used clinically.

Another technique for correcting metal artifacts includes performing "projection completion" whereby a corrupted portion of a projection is "completed" or replaced with synthetic projection data having more favorable properties. A shortcoming of projection completion methods is robustness in terms of differing reconstruction parameters (e.g., fields of view), acquisition protocols (e.g., axial or helical), method of metal segmentation and projection interpolation, metal replacement, and the like. Furthermore, projection completion techniques are not directly applicable to multi-energy imaging.

Therefore, it would be desirable to develop an apparatus and method to reduce metal artifacts that provides consistent results using non-iterative reconstruction frameworks. Also, that addresses the above-described short-comings of projection completion methods. Furthermore, it would be desirable to design an apparatus and method for reducing metal artifacts in CT images applicable to multi-energy imaging.

BRIEF DESCRIPTION OF THE INVENTION

Embodiments of the invention are directed to a method and apparatus for reduction of metal artifacts in CT images.

Therefore, in accordance with one aspect of the invention, a computer readable storage medium has stored thereon a computer program comprising instructions, which, when executed by a computer, cause the computer to acquire a first view dataset based on x-rays received by a detector corresponding to a first energy level, reconstruct an initial image using the first view dataset, the initial image comprising a plurality of metal voxels at respective metal voxel locations, and generate a metal mask corresponding to the plurality of metal voxels within the initial image. The instructions also cause the computer to forward project the metal mask onto the first view dataset to identify metal dexels in the first view dataset, perform a weighted interpolation based on the identified metal dexels to generate a completed first view dataset, reconstruct a first final image using the completed first view dataset, the first final image comprising a plurality of image voxels corresponding to the metal voxel locations, and replace a portion of the plurality of image voxels corresponding to the metal voxel locations with smoothed metal values.

In accordance with another aspect of the invention, a method includes reconstructing an image using an imaging dataset based on x-rays received by a detector corresponding to a first energy level, generating a metal mask from the image corresponding to metal voxel locations within the imaging dataset, and forward projecting the metal mask onto the imaging dataset. The method also includes identifying a plurality of metal dexels and a plurality of non-metal dexels within the imaging dataset based on the metal mask, removing the plurality of metal dexels from the imaging dataset, and generating a plurality of interpolated dexels via a weighted interpolation algorithm. The method further includes replacing each of the plurality of metal dexels in the imaging dataset with a respective interpolated dexel of the plurality of interpolated dexels, reconstructing a final image using the plurality of non-metal dexels and the plurality of interpolated dexels, and smoothing image voxels in the final image corresponding to the metal voxel locations.

In accordance with another aspect of the invention, an imaging system includes a rotatable gantry having an opening for receiving an object to be scanned, and an x-ray source coupled to the gantry and configured to project x-rays through the opening. The imaging system also includes a generator configured to energize the x-ray source to a first energy level to generate x-rays corresponding to the first energy level, a detector having pixels therein, the detector attached to the gantry and positioned to receive x-rays projected from the x-ray source, and a computer. The computer is programmed to access a first projection dataset corresponding to the first energy level, reconstruct a first image from the first projection dataset, and segment the first image to identify metal locations. The computer is also programmed to forward project the segmentation onto the first projection dataset to identify a plurality of metal detector pixels in the first projection dataset, remove the plurality of metal detector pixels from the first projection dataset, and use a weighted interpolation to replace the removed plurality of metal detector pixels and to complete the first projection dataset. Further, the computer is programmed to reconstruct a completed first image using the completed first projection dataset and smooth portions of the completed first image corresponding to the metal locations of the first energy image.

Various other features and advantages will be made apparent from the following detailed description and the drawings.

BRIEF DESCRIPTION OF THE DRAWINGS

The drawings illustrate preferred embodiments presently contemplated for carrying out the invention.

In the drawings.

DETAILED DESCRIPTION

The operating environment of embodiments of the invention is described with respect to a sixty-four-slice computed tomography (CT) system. However, it will be appreciated by those skilled in the art that embodiments of the invention are equally applicable for use with other multi-slice configurations. Moreover, embodiments of the invention will be described with respect to the detection and conversion of x-rays. However, one skilled in the art will further appreciate that embodiments of the invention are equally applicable for the detection and conversion of other high frequency electromagnetic energy. Embodiments of the invention will be described with respect to a "third generation" CT scanner, but is equally applicable with other CT systems as well as vascular and surgical C-arm systems and other x-ray tomography systems.

Figure 1:
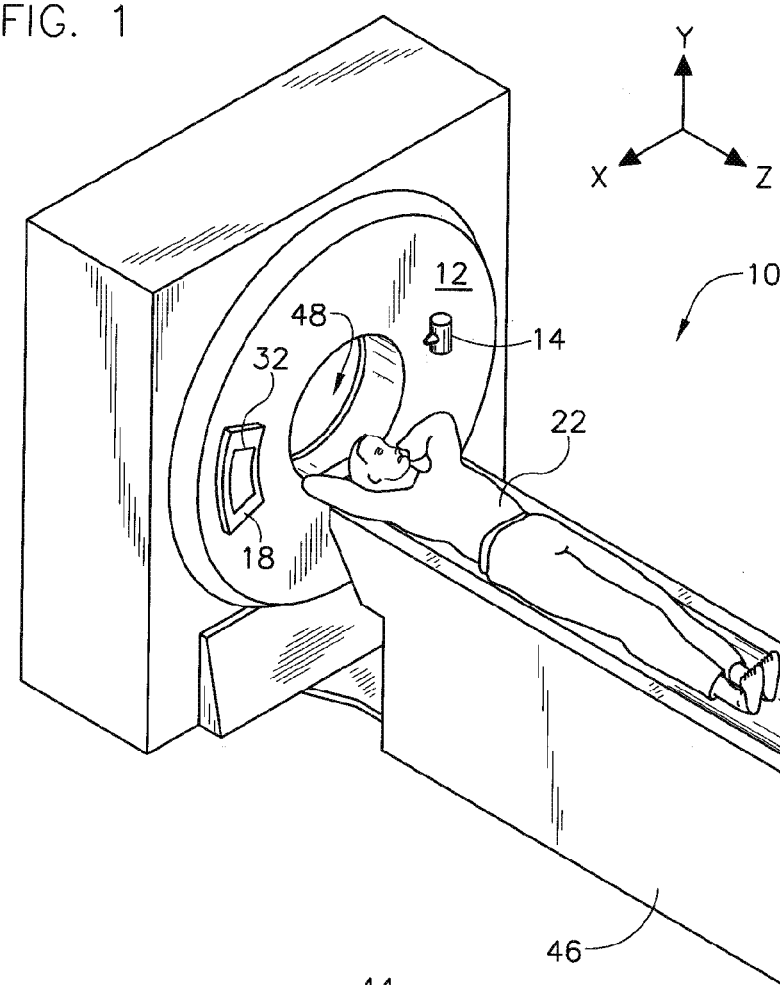
FIG. 1 is a pictorial view of a CT imaging system.
Figure 2:
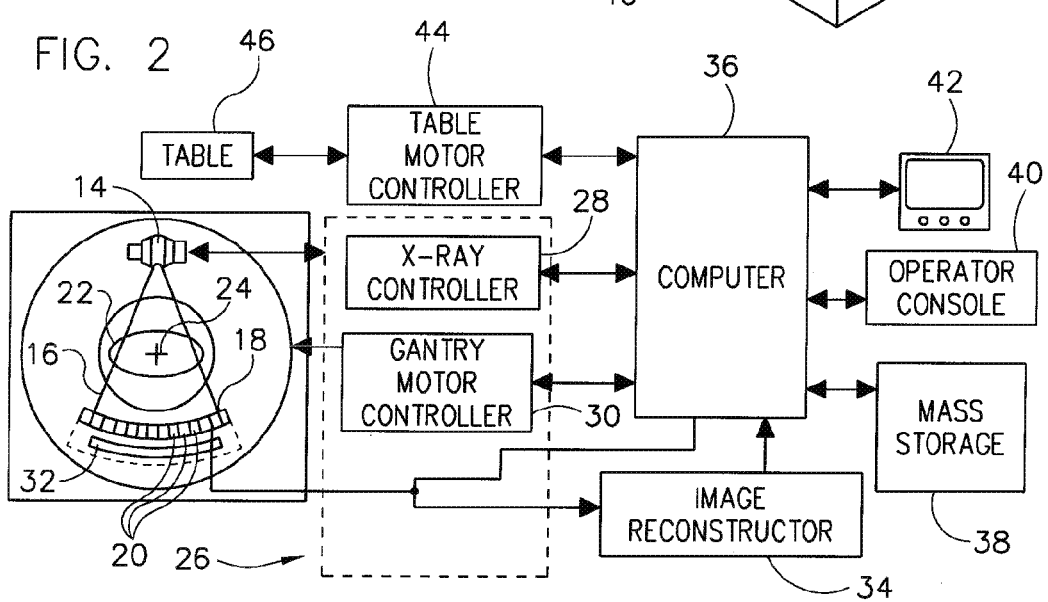
FIG. 2 is a block schematic diagram of the system illustrated in FIG. 1.

Referring to FIG. 1, a computed tomography (CT) imaging system 10 is shown as including a gantry 12 representative of a "third generation" CT scanner. Gantry 12 has an x-ray source 14 that projects a beam of x-rays toward a detector assembly or collimator 18 on the opposite side of the gantry 12. Referring now to FIG. 2, detector assembly 18 is formed by a plurality of detectors 20 and data acquisition systems (DAS) 32. The plurality of detectors 20 sense the projected x-rays 16 that pass through a medical patient 22, and DAS 32 converts the data to digital signals for subsequent processing. Each detector 20 produces an analog electrical signal that represents the intensity of an impinging x-ray beam and hence the attenuated beam as it passes through the patient 22. During a scan to acquire x-ray projection data, gantry 12 and the components mounted thereon rotate about a center of rotation 24.

Rotation of gantry 12 and the operation of x-ray source 14 are governed by a control mechanism 26 of CT system 10. Control mechanism 26 includes an x-ray controller 28 that provides power and timing signals to an x-ray source 14 and a gantry motor controller 30 that controls the rotational speed and position of gantry 12. An image reconstructor 34 receives sampled and digitized x-ray data from DAS 32 and performs high speed reconstruction. The reconstructed image is applied as an input to a computer 36 which stores the image in a mass storage device 38.

Computer 36 also receives commands and scanning parameters from an operator via console 40 that has some form of operator interface, such as a keyboard, mouse, voice activated controller, or any other suitable input apparatus. An associated display 42 allows the operator to observe the reconstructed image and other data from computer 36. The operator-supplied commands and parameters are used by computer 36 to provide control signals and information to DAS 32, x-ray controller 28 and gantry motor controller 30. In addition, computer 36 operates a table motor controller 44 which controls a motorized table 46 to position patient 22 and gantry 12. Particularly, table 46 moves patients 22 through a gantry opening 48 of FIG. 1 in whole or in part.

Figure 3:
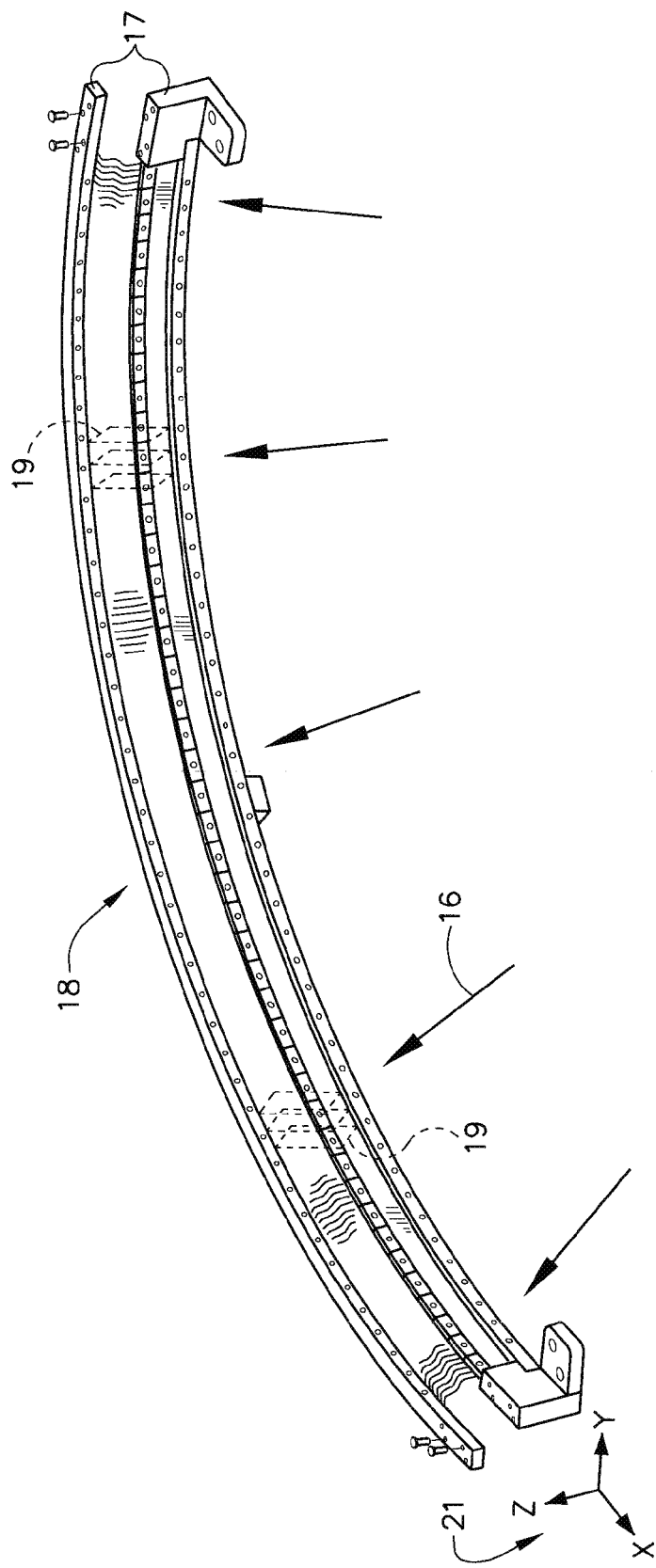
FIG. 3 is a perspective view of one embodiment of a CT system detector array.

As shown in FIG. 3, detector assembly 18 includes rails 17 having collimating blades or plates 19 placed therebetween. Plates 19 are positioned to collimate x-rays 16 before such beams impinge upon, for instance, detector 20 of FIG. 4 positioned on detector assembly 18. In one embodiment, detector assembly 18 includes fifty-seven detectors 20, each detector 20 having an array size of 64×16 of pixel elements 50. As a result, detector assembly 18 has sixty-four rows and nine hundred twelve columns (16×57 detectors) which allows sixty-four simultaneous slices of data to be collected with each rotation of gantry 12.

Figure 4:
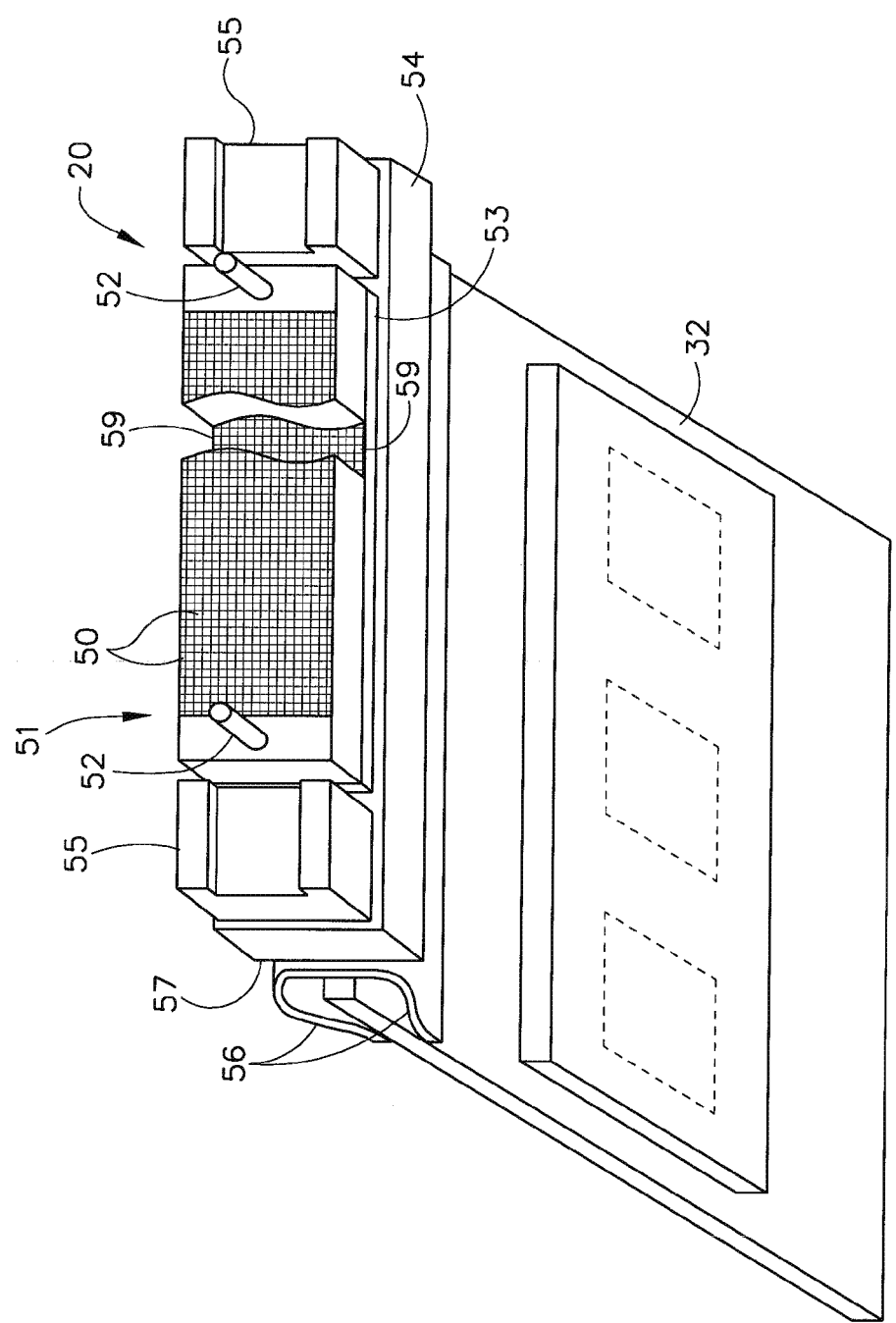
FIG. 4 is a perspective view of one embodiment of a detector.

Referring to FIG. 4, detector 20 includes DAS 32, with each detector 20 including a number of detector elements 50 arranged in pack 51. Detectors 20 include pins 52 positioned within pack 51 relative to detector elements 50. Pack 51 is positioned on a backlit diode array 53 having a plurality of diodes 59. Backlit diode array 53 is in turn positioned on multi-layer substrate 54. Spacers 55 are positioned on multi-layer substrate 54. Detector elements 50 are optically coupled to backlit diode array 53, and backlit diode array 53 is in turn electrically coupled to multi-layer substrate 54. Flex circuits 56 are attached to face 57 of multi-layer substrate 54 and to DAS 32. Detectors 20 are positioned within detector assembly 18 by use of pins 52.

In the operation of one embodiment, x-rays impinging within detector elements 50 generate photons which traverse pack 51, thereby generating an analog signal which is detected on a diode within backlit diode array 53. The analog signal generated is carried through multi-layer substrate 54, through flex circuits 56, to DAS 32 wherein the analog signal is converted to a digital signal.

Figure 5:
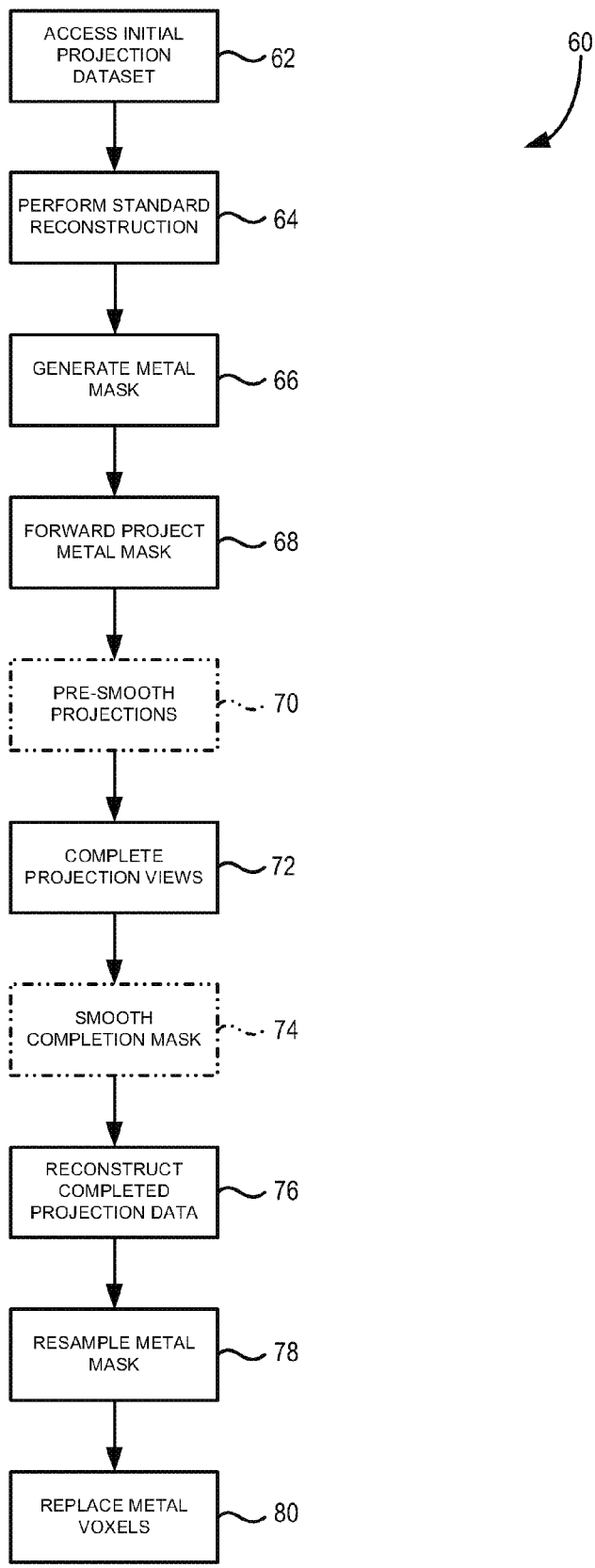
FIG. 5 is a flowchart illustrating a technique for reducing metal artifacts according to embodiments of the invention.

Referring now to FIG. 5, a metal artifact reduction technique 60 is set forth according to an embodiment of the invention. As discussed in detail below, technique 60 acquires or accesses an initial projection dataset or initial view dataset and performs a standard reconstruction of the initial projection dataset to generate an initial reconstructed CT image dataset. A metal mask is generated by first applying a threshold to the reconstructed image dataset and subsequently optionally applying morphological operations to modify the mask. The metal mask is used to indicate locations of metal voxels within the image dataset. The metal mask is forward projected onto the projection data to identify detector pixels containing metal, or dexels, in the initial view dataset. All detectors cells marked as being impacted by the metal mask are completed via a weighted three-dimensional interpolation. An optional smoothing is applied to the interpolated patch before replacing the metal dexels in the initial view dataset with the completed patch. The completed projection data is reconstructed to generate a final CT image dataset. Because former metal voxels may be improperly represented in the final CT image dataset, the metal voxels are replaced in the final CT image dataset with modified and smoothed image voxels corresponding to the metal voxel locations. In a multi-energy context, the projection interpolation, interpolation patch smoothing, and metal replacement may be applied in a joint fashion to preserve the physical meaning of the BMD images.

Technique 60 begins by accessing an initial projection dataset at step 62. The initial projection dataset may be accessed from a storage location or from a live or real-time scan. At step 64, technique 60 performs a standard reconstruction of projection data to generate an initial reconstructed CT image dataset. According to embodiments of the invention, one or multiple sets of images may be reconstructed from any of high-energy images, low-energy images, monochromatic images (at any keV level), images blended in any combination of high and low energy images, and material basis images or material decomposed images (of any material basis combination).

The initial CT image dataset includes a number of reconstructed image slices corresponding to parameter set "A." According to one embodiment, the initial reconstruction is performed with centered targeting and a full display field of view (e.g., 500 mm) to increase the probability of capturing metal in the reconstructed volume. That is, the field of view and target center for the initial reconstruction may differ from the field of view and target center for the final reconstruction, which will be reconstructed with parameter set "B." Also, any fixed reconstruction kernel may be used so the metal mask does not depend on a user-specified reconstruction kernel. Thus, the generated metal mask will not be affected if, for example, the user changes the reconstruction kernel. For cases including a tilted gantry, the initial reconstruction may also be performed assuming a gantry tilt value of zero so that the forward projector does not need to account for gantry tilt. Other embodiments may account for gantry tilt directly in the forward projector.

For helical scanning applications, images are reconstructed at the same z locations as the original request, according to one embodiment. Alternatively, additional z slices, or z slices with different spacing may be reconstructed to increase the probability of fully covering any metal objects or for the purpose of yielding a more refined metal mask.

For axial scanning applications, additional slices may be reconstructed outside of the standard image volume range or primary reconstruction volume in a direction orthogonal to the axial scan plane (i.e., in the z-direction). The additional slices are reconstructed to acquire non-primary reconstruction data and determine the location of metal outside the primary reconstruction region that may still be incident upon the detector during the acquisition. Specifically, x-ray paths with larger cone angles may pass through areas of an object that are not covered by the standard image volume. If the x-ray path that propagates through metal is not in the standard reconstruction volume, but the projection of the metal is still present in the views, the dexels may not be correctly identified by the forward projection procedure. These unlabeled dexels may potentially be identified as valid values during projection completion, thereby re-introducing metal into the completed view and causing artifacts. According to one embodiment, sixty-four slices may be reconstructed for a 32 slice scan, and ninety-six slices may be reconstructed for a 64 slice scan. However, one skilled in the art will recognize that any number of additional slices may be reconstructed based on clinical experience. In one embodiment, corresponding view-weighting parameters are applied to the additional slices. The view-weighting parameter is based on the image z-offset from the central scan plane and is symmetric about the scan plane. However, one skilled in the art will recognize that different values of view-weighting can be used based on clinical experience.

At step 66, technique 60 segments each image of the initial CT image dataset using a threshold value to indicate metal voxels within the image dataset. As used herein, the term "metal" is used to denote objects or voxels in the image corresponding to high x-ray attenuation properties even if those objects are not metal. The segmentation generates a binary metal mask by applying the threshold to the reconstructed image dataset and inserting any voxels above the threshold value into the metal mask.

Optionally, the binary metal mask may be further processed using dilations and erosions in order to remove small pieces of metal from the mask and slightly expand the metal region, thus preventing partial voluming effects. An erosion operation removes a voxel from the metal mask if greater than $T_e$ of its neighboring voxels are not in the metal mask. A dilation operation inserts a voxel into the metal mask if greater than $T_d$ of its neighbors are in the metal mask. According to one embodiment, $N_e$ erosion iterations are applied to the metal mask, followed by $N_d$ dilation iterations. By applying the erosions first, some or all small metal features are eliminated from the metal mask under the assumption that x-rays have penetrated a small object and thus there is no photon starvation 'behind' the small piece of metal. Following the erosion process, the first $N_e$ dilations reinsert most of the original metal mask voxels into the updated metal mask. However, the small regions or metal features eliminated by the erosions are not reintroduced. The remaining $N_d-N_e$ dilations expand the metal mask region and fill in holes. $N_d$ may be larger or smaller than $N_e$. Furthermore, $N_d$ and $N_e$ may assume any integer value. This optional procedure of further processing using dilations and erosions helps to prevent streak artifacts resulting from not including metal voxels from the initial reconstructed CT image dataset in the metal mask during the initial segmentation.

The neighborhood of a voxel for the erosion and dilation operations may be defined in a variety of ways. According to embodiments of the invention, these neighborhoods can be defined as any combination of sets of 2D or 3D neighbors. For example, according to one embodiment, erosions are performed among the eight nearest in-plane neighbors (i.e., a 2D neighborhood), and dilations are performed among the twenty-six nearest 3D neighbors (i.e., a 3D neighborhood).

The values of $T_e$ and $T_d$ may be functions of the neighborhood definitions. In one embodiment, both $T_e$ and $T_d$ are zero so that an erosion operation removes a voxel from the metal mask if any of its neighbors are not in the metal mask and a dilation operation inserts a voxel into the metal mask if any of its neighbors are in the metal mask.

At step 68, the metal mask is forward projected onto the initial projection dataset. Specifically, the metal voxels, which may be indicated by non-zero values in the binary metal mask, are projected onto the detector for a given source position. Those detector pixels or dexels that have a non-zero contribution from the forward projection are labeled as metal detector pixels or metal dexels.

According to one embodiment, in a dual energy imaging procedure, technique 60 assumes that the image datasets corresponding to each energy level have projections at an identical set of view angles. That is, technique 60 assumes the two datasets are registered with one another. Thus, the same metal mask is forward projected onto each view angle of both energy datasets.

According to one embodiment, the forward projection of step 68 is performed with a pixel-driven approach that accounts for the "spread" of a given voxel onto the detector for a given source position. First, the detector coordinate intersection for the ray connecting the source position and the voxel center is calculated, similar to pixel-driven back projection. This detector coordinate intersection point may be defined as u in units of detector channels. However, instead of labeling only the four nearest dexels using an analogue to bilinear interpolation-based backprojection, the spread calculation correctly labels the full range of dexels impacted by this metal voxel as metal dexels. Otherwise, a metal dexel may be potentially skipped over because the dexel is not one of the nearest four dexels to the detector intersection point u. That is, if two consecutive voxels are marked as metal in the metal mask, projecting them to the detector using a bilinear interpolation approach may leave an unlabeled dexel between two pairs of dexels labeled from the voxel projections even though the labeled metal dexels should be contiguous.

In one embodiment, the spread may be calculated based upon a magnification factor, mag, applied to the most orthogonal axis (x or y) of the current voxel from the perspective of the ray connecting the source and voxel center. The magnification factor can be defined as the distance from the source to the current voxel center divided by the distance from the source to the detector. The angle θ is determined between the source and current voxel center and the positive y-axis. The spread s of the current metal voxel on the detector is then given by:

$$s = \begin{cases} mag \cdot \Delta x \cdot |\cos(\theta)| : & |\cos(\theta)| > |\sin(\theta)| \\ mag \cdot \Delta y \cdot |\sin(\theta)| : & \text{otherwise,} \end{cases} \quad \text{(Eqn. 1)}$$

where $\Delta x$ and $\Delta y$ define the width and height of the voxels, respectively. The detector channel range is then given by $[u_{min}, u_{max}]$ where $u_{min} = u - s/(2\Delta u)$, $u_{max} = u + s/(2\Delta u)$, and $\Delta u$ is the width of a detector channel.

The detector coordinate range in the z-direction is also calculated, by first computing the detector row intersection point, v, in units of detector rows for the ray connecting the source and the voxel center. The row spread is then defined by the range $[v_{min}, v_{max}]$ where detector height, $\Delta v$, the z projection of the voxel center onto the detector is given by:

$$v_{min} = v - 0.5 D \Delta z/(d\Delta v)$$

$$v_{max} = v + 0.5 D \Delta z/(d\Delta v) \quad \text{(Eqn. 2)},$$

where $\Delta z$ is the non-negative slice spacing, $\Delta v$ is the height of the detector row, d is the in-plane source to voxel center distance (i.e., the distance in the x and y directions, but not the z direction), and D is the source to detector distance. While these calculations may assume a specific system geometry (e.g., a detector with no curvature in z), one skilled in the art could adapt the calculations for a different geometry.

According to another embodiment, the forward projection of step 68 projects the eight voxel corners onto the detector to yield eight detector intersection points. The values $u_{min}$ and $u_{max}$ are then the minimum and maximum detector channel intersection points, respectively, in the set of eight intersection points. Similarly, the $v_{min}$ and $v_{max}$ values are then minimum and maximum detector row intersection points, respectively.

Finally, all dexels in the calculated range are labeled as metal dexels. Specifically, a dexel with channel $c_i$ and row $r_j$ is marked as a metal dexel if $\lfloor u_{min} \rfloor \leq c_i \leq \lfloor u_{max} \rfloor$ and $\lfloor v_{min} \rfloor \leq r_j \leq \lfloor v_{max} \rfloor$ where $\lfloor x \rfloor$ is the floor operation.

Some forward projected rays may extend outside of the available reconstructed volume in the z direction prior to intersecting the detector. As noted above with respect to the generation of additional image slices for the axial case, unidentified metal in the z direction may cause problems during the projection interpolation. In one embodiment, these problems may be addressed by padding the image volume such that the edge slices are replicated, extrapolated from existing slices, or based upon prior knowledge, including anatomical knowledge or a scout scan. In another embodiment, the forward projector may account for this directly. Specifically, if a metal voxel in an edge slice of the image volume forward projects onto the detector, then $v_{min}$ or $v_{max}$ is extended to the edge of the detector in the same direction as would be used if the edge slice were replicated.

At step 70 (shown in phantom), technique 60 applies optional pre-smoothing to the projection data to reduce streaking. In one embodiment, pre-smoothing can be applied as a weighted average of a given neighborhood of a dexel that will be used during the interpolation. The neighborhood may be defined in one, two, or three dimensions and the weights may depend on the distances to the neighbors, the total number of available neighbors, and/or the amount of smoothing desired. Thus, the pre-smoothing takes the form:

$$\hat{d}_{i,j,k} = \sum_{(i',j',k') \in N_{i,j,k}} \left( \frac{\alpha(i',j',k')}{\sum_{(i'',j'',k'') \in N_{i,j,k}} \alpha(i',j',k')} \right) d_{i',j',k'}, \quad \text{(Eqn. 3)}$$

where $N_{i,j,k}$ is the set of valid (i.e., non-metal or previously completed) voxels in a neighborhood of voxel (i,j,k) and $\alpha$ is a weight that depends on the voxel (i', j', k'). In the case that no valid neighbors are available, the pre-smoothing has no effect.

Technique 60 completes or replaces all detectors cells marked as being impacted by the metal mask via a weighted interpolation at step 72. The completion step interpolates in row, channel, and view directions using valid neighbors of a metal dexel that are not metal dexels, assigns weights to each of the neighbors, and replaces the metal dexel by the sum of the weighted neighbors. In addition, previously completed projection data can be used when interpolating in the view direction. For dual kVp imaging, technique 60 applies identical interpolation coefficients to replace corresponding elements of views acquired or synthesized at multiple energies.

In one embodiment, the interpolation used to replace the metal dexel $d_{i,j,k}$ given by channel i, row j, and view k takes the form:

$$\hat{d}_{i,j,k} = W_c C + W_R R + W_V V \quad \text{(Eqn. 4)}$$

where $W_c$, $W_R$, and $W_V$ represent weighting values in the channel, row, and view direction, respectively. Furthermore, C, R, and V represent contributions from the channel, row, and view directions, where C, R, and V can depend on any of the available projection data, including previously completed values.

A binary mask, U, is defined such that $U_{i,j,k}$ has a value of one if dexel $d_{i,j,k}$ is a metal dexel and zero otherwise. Further, the nearest neighbors of metal voxel $d_{i,j,k}$ that are not metal dexels in the channel, row, and view directions are defined as $i_1, i_2, j_1, j_2, k_1, k_2$, respectively. For example, $i_1$ may be defined as the largest index such that $i_1 < i$ and $U_{i1,j,k}=0$. Similarly, $i_2$ may be defined as the smallest index such that $i_2 > i$ and $U_{i2,j,k}=0$. Neighbor indices for the row and view directions (i.e., $j_1$, $j_2$, $k_1$, and $k_2$) may be defined in a similar manner. Some values may be undefined if there are no non-metal dexels in a certain direction (e.g., if off the edge of the detector in the channel and row case or if all dexels in a given direction are metal dexels). Furthermore, maximum distances can be defined in the row, channel, and view directions so that neighbors are undefined if the nearest valid neighbor would exceed the maximum distance for that direction. Other embodiments may include additional neighbors in each direction for use with higher-order interpolation strategies.

With respect to the historical view data $d_{i,j,k1}$, for all views after the first view, the dexel (i,j) in the previous view is either not a metal dexel or has already been completed. Thus $k_1$ is k−1 except for the first view where $k_1$ is undefined. However, the age of dexel (i, j) (i.e., the number of views since a given dexel was not a metal dexel) can also be used for weighting during the interpolation. Other embodiments may use the last non-metal historical dexel directly rather than the potentially previously completed dexel from the prior view.

Interpolated values for channel ($I_c$), row ($I_r$), and view ($I_v$) are defined as follows:

$$I_c = \alpha_{11} \hat{d}_{i1,j,k} + \alpha_{12} \hat{d}_{i2,j,k}$$

$$I_r = \alpha_{21} \hat{d}_{i,j1,k} + \alpha_{22} \hat{d}_{i,j2,k}$$

$$I_v = \alpha_{31} \hat{d}_{i,j,k1} + \alpha_{32} \hat{d}_{i,j,k2} \quad \text{(Eqn. 5)}.$$

According to one embodiment, $$\alpha_{11} = 1 - \alpha_{12}, \alpha_{12} = \frac{i - i_1}{i_2 - i_1},$$

$$\alpha_{21} = 1 - \alpha_{22}, a_{22} = \frac{j - j_1}{j_2 - j_1},$$

and $\alpha_{31} = 1 - \alpha_{32}, \alpha_{32} = \frac{k_2 - k}{A_{i,j,k} + k_2 - k}$, where $A_{i,j,k}$ is the age of dexel (i,j) in view k. Ages may be initialized to an arbitrary value, for example, $A_{init}=100$, for use before a valid dexel is available. Other embodiments may include higher-order interpolation if additional neighbors are available in a given direction, different interpolation coefficients, or alternate historical view weighting strategies.

The interpolated values $I_c$, $I_r$, $I_v$ apply where two neighbors exist in a given direction from which to interpolate. If only a single neighbor is available in a single direction, that single neighbor value is used for that direction. If no neighbors are available in a given direction, that direction is not used in the interpolation. The interpolated values $I_c$, $I_r$, $I_v$ depend on dexel indices i, j, k. However, the indices are assumed fixed here forth for purposes of explanation.

The interpolated values in each direction are combined according to weighting functions, W, based on a distance, D, calculated for that direction. The distance function may differ for the cases when one or two valid neighbors is available. Specifically, distances are defined by:

$$D_O(v_1, E, v) = |v_1 - v| \sqrt{|E - v_1|}$$

$$D_T(v_1, v_2, v) = \min(\hat{v}_1, \hat{v}_2) \sqrt{\max(\hat{v}_1, \hat{v}_2)} \text{ where } \hat{v}_1 = \min$$
$$(|v_1 - v|, \text{CLIP}) \text{ and } \hat{v}_2 = \min(|v_2 - v|, \text{CLIP}) \quad \text{(Eqn. 6)},$$

where α, β, and λ denote scaling factors to adjust the relative weights of the row, channel, and view directions, $D_T$ is a two-sided distance (i.e., involving two neighbors), $D_O$ is a one-sided distance (i.e., involving one valid neighbor), E indicates an 'edge' value on the opposite side of the one valid value (i.e., E is −1 or one past the last possible row, channel, or view), and CLIP is a clipping threshold. These distance calculations account for the fact that the previous interpolations in the given directions will be more accurate in the case when one of the distances is small, while also not too heavily penalizing the case that only one of the distances is large. The distances in the channel, row, and view direction may then be composed using these distance functions. For example, assuming the two-sided distance function is applicable, the channel, row, and view distance functions are given by:

$$D_c = \alpha D_T(i_1, i_2, i)$$

$$D_r = \beta D_T(j_2, j_1, j)$$

$$D_v = \lambda D_T(-A_{i,j,k}, k_2 - k, 0) \quad \text{(Eqn. 7)},$$

where α, β, and λ denote scaling factors to adjust the relative weights of the row, channel, and view directions. For other embodiments, different distance definitions may be used. The weightings α, β, and λ can be used where data is expected to be more reliable in some direction due, for example, to anatomical knowledge, reconstruction parameters, a-priori information such as a scout scan, or known clinical scenarios.

With these distance metrics defined, according to one embodiment, the weighting functions, W, are given as:

$$W_C(C, R, V) = \frac{(1/C)}{(1/C) + (1/R) + (1/V)} \quad \text{(Eqn. 8)}$$

$$W_R(C, R, V) = \frac{(1/R)}{(1/C) + (1/R) + (1/V)}$$

$$W_V(C, R, V) = \frac{(1/V)}{(1/C) + (1/R) + (1/V)}$$

where C, R, and V are distance metrics computed in the channel, row, and view directions. Each of C, R, and V may be based on a two-sided distance, a one-sided distance, or not be available. In cases where the values are not available due to the lack of valid neighbors, the weighting equations are adjusted accordingly.

After generating the completion mask, technique 60 optionally smoothes the completion mask at step 74 (shown in phantom) to prevent steaks in the resulting images due to sharp changes in value from one dexel to the next. Only metal dexels are smoothed at step 74. The completion smoothing applies zero or more convolutions for each of the completed metal dexels. In one embodiment, the convolution is 2D (i.e., in channel and row, but not in view), but a 3D convolution can also be used to smooth in view. The convolution coefficients can be tuned and selected based on clinical experience, anatomical regions, reconstruction parameters, or a-priori information such as a scout scan. Although some of the neighboring dexels may be metal dexels, all metal dexels have been completed and are thus valid for use in smoothing.

According to one embodiment, smoothing is carried out in the row and channel directions. For example, dexels $\{d_{i\pm 1, j\pm 1, k}\}$ may be used to smooth dexel $d_{i,j,k}$. If dexel $d_{i,j,k}$ is on an edge of the detector, some neighboring dexels may not be defined. If such is the case, dexel $d_{i,j,k}$ is replaced with:

$$d'_{i,j,k} = c \cdot d_{i,j,k} + \sum_{m=1}^{m=|N|} N_m \frac{1-c}{|N|}, \quad \text{(Eqn. 9)}$$

where N is the set of all defined neighbors, |N| is the number of defined neighbors, $N_m$ is the m-th neighbor, and c is the weight assigned to dexel $d_{i,j,k}$. Alternatively, smoothing could be carried out in all three directions and with differently defined neighborhoods and smoothing coefficients.

According to one embodiment, the completion smoothing may be applied iteratively, by providing the result of the prior smoothing iteration as an input. Alternatively, the completion smoothing may be omitted.

At step 76, technique 60 reconstructs the completed projection data to generate a final CT image dataset. The image voxels of the final CT image dataset are now marked in the final CT image dataset because the reconstructed values are not correct. Specifically, former metal voxels may appear washed out in the final CT image dataset or be incorrectly scaled in the case of material basis images.

According to one embodiment, technique 60 replaces the values of image voxels that are former metal voxels in a set of material basis images, such as, for example, water and iodine images. The former metal voxels are replaced such that the resulting monoenergetic images behave as expected for some assumed material (e.g., titanium) when the material basis images are combined. That is, as the monoenergetic energy increases, the attenuation of the material decreases in accordance with an assumed attenuation curve of the material. The method of choosing the voxels in the image dataset reconstructed in step 76 may vary. In one embodiment, a threshold is applied to the calculated fractions, $f_k$, to generate a binary metal mask for the final reconstructions. In this embodiment, a threshold, t, is defined for the fractional metal coverage values above which a voxel is considered to be metal and will be replaced.

To replace the former metal voxels in the material basis images, technique 60 performs a least squares fit between the per-keV attenuation coefficient calculated from the material basis images and the expected values for the assumed metal material. For example, technique 60 may perform a least squares fit between water-iodine ratios and titanium-water ratios over a range of energies to provide water and iodine replacement values that behave as expected for titanium over a relevant keV range. The least squares fit can be weighted to enforce a closer match at some specified keV, such as, for example, 70 keV. The resulting weighted values can then be scaled such that the monoenergetic value at the specified keV matches the original metal threshold value or some other expected or desired value. This weighting and scaling procedure generates a constant value that is used to replace the metal voxels from the initial reconstruction. For a single energy case or single energy images from a multi-energy case, on the other hand, technique 60 may use a metal threshold or a constant value to replace the metal voxels. In either case, lookup table or an adaptive threshold based on information determined within the scan may be used to create the replacement value.

Because the final reconstruction parameter set "B" may differ from the initial reconstruction parameter set "A" (in field of view, target centering, slice spacing, and gantry tilt, for example), technique 60 re-samples the metal mask generated from the initial CT image dataset to the geometry of the final CT image dataset at step 78.

In one embodiment, at step 78, technique 60 calculates the fraction of the volume of each voxel in the final reconstruction that is "covered" by metal voxels in the original metal mask. The calculated fractions indicate how much of each newly reconstructed voxel was labeled as metal in the initial reconstruction.

The total volumetric intersection between the metal voxels in the first reconstruction and the $k^{th}$ voxel in the final reconstruction is defined as:

$$v_k = \sum_{i \in N'} |x'_i \cap x_k| \cdot |y'_i \cap y_k| \cdot |z'_i \cap z_k|, \quad \text{(Eqn. 10)}$$

where $x_k$ denotes the range of x values covered by voxel k, $a \cap b$ denotes the intersection of two ranges, $|x_k|$ denotes the length of an interval, N' is the set of indices of non-zero metal mask voxels in the first reconstruction and x', y', and z' are coordinates in the first reconstruction. Similar definitions hold for $y_k$, $|y_k|$, $z_k$, and $|z_k|$. Thus, the fraction, $f_k$, of the $k^{th}$ voxel that is covered by metal in the new reconstruction is:

$$f_k = \frac{v_k}{|x_k| \cdot |y_k| \cdot |z_k|}.$$ (Eqn. 11)

The calculated fractions, $f_k$, are used to determine metal replacement values, as described below. According to one embodiment, technique 60 re-samples the original metal mask and not the mask generated after applying morphological operations to the original. Another embodiment reapplies the morphological operations to the initial metal mask, but with different neighborhoods. For example, with initial neighborhoods of 2D and 3D for the erosions and dilations, respectively, the erosions and dilations can both be reapplied to the original mask with 2D neighborhoods and the result used for the mask re-sampling step.

For cases including gantry tilt, according to embodiments of the invention where the initial reconstruction was performed with the assumption of no gantry tilt, re-sampling can take into account the fact that the y positioning of the z slices may differ between the initial and final reconstructions. In alternative embodiments, the initial reconstruction may take into account the gantry tilt.

Technique 60 smoothes the replaced metal voxels in the final CT image dataset with smoothed metal values at step 80. According to one embodiment, technique 60 applies a smoothing function based on the fraction of a given neighborhood around the voxel to be replaced that includes metal. The set of voxels to be replaced within a given neighborhood of the voxel to be replaced are defined as $D_c$. Then the fraction of the neighborhood covered by metal is calculated as:

$$F_c = \frac{\sum_{k \in D_c} f_k}{|D_c|},$$ (Eqn. 12)

where $|D_c|$ is the volume or area of the neighborhood and $f_k$ is given above. Further the set of voxels that will not be replaced, $D_n$, is given as:

$$D_n = \{k \in D_c | f_k < t\}$$ (Eqn. 13)

for some threshold t.

The mean, u, of the reconstructed values, $I_k$, represented by voxel indices in $D_n$ is calculated. If every voxel in the neighborhood will be replaced by metal (i.e., $D_n$ is empty) then the mean, u, is set to a metal replacement value, m, as described above.

Technique 60 interpolates between u and m using an interpolation coefficient based on $F_c$. According to one embodiment, $F_c^n$ is used as the interpolation coefficient to control the relative contribution from the values u and m. The initially reconstructed value, $I_k$, is replaced with a smoothed replacement value, $I'_k$ according to:

$$I'_k = (1 - F_c^n)u + F_c^n m$$ (Eqn. 14)

for some value of n.

According to one embodiment, the neighborhood that determines $D_c$ is defined based on a radial distance. In particular, voxels whose centers lie within some distance r of the center of the voxel to be replaced are included in $D_c$. This radial distance can be applied in-plane (i.e, a disc in 2D) or volumetrically (i.e., a sphere in 3D). Other embodiments could include different (e.g., non-radial) neighborhoods.

For the dual energy imaging case, technique 60 may jointly apply the above-described smoothing operation on both basis images near the edges of the replaced metal region to smooth the appearance of the replacement mask. According to one embodiment, identical weighting is applied to both material basis images so that the smoothed weighted region behaves as expected when performing subsequent basis image combinations. After the replaced metal voxels in the final CT image dataset are smoothed, technique 60 may form new images as weighted combinations of low and high kV energy images or material decomposed images.

According to another embodiment of the invention, replacement of metal voxels may be performed directly in images formed by weighted combinations of a given set of available energy and material basis images. Further, the weighted smoothing operation may be applied directly to the metal mask in the weighted combination images.

Embodiments of the interpolation technique described with respect to FIG. 5 may use fixed directions with distance-based weighting. Alternatively, an initial image with metal removed may be forward projected to yield per-dexel estimates of the expected projection values, as described in detail below with respect to FIG. 6. These forward projected values may then be used to guide the interpolation by providing additional information. For example, the forward projection may indicate that a metal dexel is expected to be most similar to non-metal dexels along a different direction than the fixed interpolation. In that case, performing the interpolation in the direction indicated by the forward projection should improve the quality of the final image. Metal voxels corresponding to metal locations identified in the CT image dataset may be replaced with nearby non-metal voxels (e.g., voxels corresponding to tissue or water locations) or a constant (e.g., water) prior to performing forward projection. By synthesizing values in the metal replacement region prior to forward projection, the completion of the metal regions in the projection dataset may be carried out via interpolation in any direction. The forward projection may be performed using any of the energy level images, material basis images, or monoenergetic images of a multi-energy system. Alternatively, the forward projection may be performed using a single energy (kVp) image in a conventional scanning system. This synthesizing procedure may aid in recovering edge information and prevent streaking that would otherwise be introduced in the final reconstructed image. The synthesizing procedure may also be applied after a number of iterations of a fixed-direction interpolation procedure, such as that described with respect to technique 60 of FIG. 5.

Additionally, in a dual energy imaging procedure, a low energy and a high energy image may be used to find residual artifacts and replace those values prior to forward projection. Typically, the difference in attenuation values for a given anatomy between high and low energy images falls within a given range. For example, water has approximately the same attenuation value in both high and low energy images, so the difference between the two images is approximately zero. The difference between high and low energy images for other anatomy falls within known ranges. In images with severe metal artifacts, the difference values between the high and low energy images are outside a reasonable anatomical range. Thus, by comparing high and low energy images, metal voxels corresponding to artifacts may be identified. These identified metal voxels may be replaced either via the synthesizing procedure described above or with a constant (e.g., water) prior to forward projection to prevent metal artifacts from corrupting the forward projected values.

Figure 6:
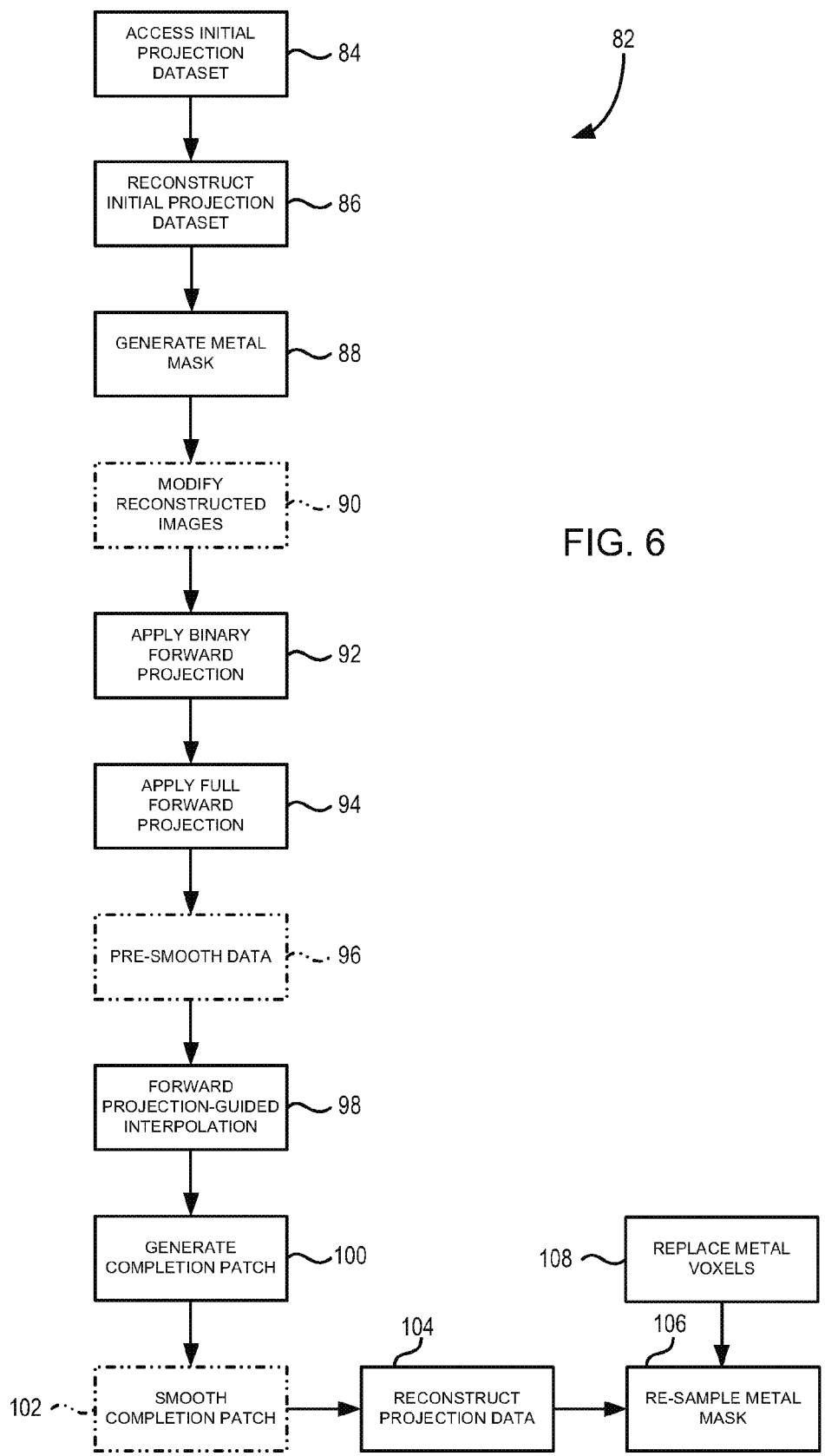
FIG. 6 is a flowchart illustrating a technique for reducing metal artifacts according to embodiments of the invention.

Referring now to FIG. 6, technique 82 may be applied to reduce metal artifacts in CT images, according to embodiments of the invention. In one embodiment, technique 82 may be applied as an alternative to technique 60 (FIG. 5). In another embodiment, technique 82 may be applied as a second pass (or one of multiple passes) after an initial application of technique 60.

Technique 82 begins by accessing an initial projection dataset at step 84. The initial projection dataset may be accessed from a storage location or in real-time during a scan. At step 86, an initial image dataset is reconstructed to generate an initial reconstruction volume. In one embodiment, an initial image dataset is reconstructed as described in step 64 of technique 60 (FIG. 5). In another embodiment, an initial image dataset is reconstructed by applying steps 62-76 of technique 60. Thus, the initial reconstruction volume may contain images from one of one or more energies, basis material decomposition images, or any combination of energy images and BMD images, with some or all of steps 62-76 of technique 60 applied to reduce metal artifacts in the initial image dataset.

Referring back to FIG. 6, after reconstructing the initial image dataset at step 86, technique 82 generates a metal mask at step 88. According to one embodiment, technique 82 generates the metal mask in a similar manner as described in step 66 of technique 60 (FIG. 5). Alternatively, if technique 60 was applied to generate the initial reconstruction, technique 82 may reuse the metal mask generated at step 66 of technique 60.

At step 90 (shown in phantom), technique 82 applies an optional modification to the images reconstructed during step 86. These original images may or may not include metal artifacts, depending on whether or not technique 60 of FIG. 5 was applied to generate the original image data set in step 86.

According to one embodiment, during step 90 the voxels identified by the metal mask generated in step 88 are replaced in the image domain to prevent a subsequent forward projection step from including metal in the forward projected data. The metal mask voxels may be replaced by a constant, such as a value to indicate water or soft tissue in one embodiment. Alternatively, the metal mask voxels may be replaced by an "image completion" process, which replaces the metal voxels by interpolations among the nearby non-metal voxels, similar to the projection domain interpolation described in step 72 (FIG. 5). In addition to interpolating nearby voxels, a constant value may also be incorporated into the interpolation. For example, the interpolation may perform a completion by considering both the weighted combination of nearby non-metal voxels and a constant such as water or soft tissue.

In another embodiment, technique 82 may additionally replace voxels that were not included in the metal mask. For example, if datasets corresponding to two energies are available, then computing the difference between one image volume and the other may indicate the location of severe reconstruction artifacts that should be corrected. Any voxel whose absolute value of the computed difference exceeds a reasonable range for expected patient anatomy or object properties may also be replaced by the image completion of step 90, as described above. The reasonable range may be fixed, may be determined based on prior knowledge (i.e., reconstruction parameters or a priori knowledge of the anatomy to be scanned), or may be determined through information obtained from a scout scan, according to embodiments of the invention. Other embodiments may apply additional morphological operations to the metal mask. For example, the metal mask may be further dilated to remove voxels that may be corrupted but are seemingly not metal. These potentially corrupt voxels are replaced, but are not considered metal voxels for the subsequent steps.

Technique 82 applies a binary forward projection operation at step 92 on the metal mask generated at step 88, such as the binary forward projection described with respect to step 68 of technique 60 (FIG. 5). As a result of applying step 92, a mask of dexels is generated "behind" the metal voxels that will be replaced during a subsequent operation. One skilled in the art will recognize that other forward projection procedures may also be used to generate a mask of metal dexels from the available metal image mask.

At step 94, technique 82 applies a full forward projection to the image volume resulting from step 90. Unlike the binary forward projection of step 92 that simply determines the dexels that have been affected by metal, the full forward projection of step 94 calculates an estimated value for a given dexel at a given view angle by forward projecting the volume from step 90.

According to one embodiment, the full forward projection of step 94 is computed using "Siddon's method," which calculates the line intersection lengths between a projection ray and each voxel and then computes the line integral of that projection ray by summing the products of the voxel values and their associated line intersection lengths. Those skilled in the art will recognize that other projection methods can also be used to estimate the projection data given the image volume from step 90.

At optional step 96 (shown in phantom), the projection data may be pre-smoothed, such as described with respect to step 70 of technique 60 (FIG. 5), where $\hat{d}_{i,j,k}$ represents the pre-smoothed projection data at index (i,j,k).

Returning to FIG. 6, at step 98, technique 82 uses the estimates generated by the forward projection in step 94 to guide an interpolation process that is used to replace the dexels indicated by the binary forward projection of step 92. Unlike the fixed projection interpolation described in step 72 of technique 60 (FIG. 5), the forward projection-guided interpolation of step 98 may adaptively determine the directions along which it will interpolate. According to embodiments of the invention, step 98 may use a portion of the forward projection values computed by step 94. Thus, step 94 may restrict the forward projection to the projection rays that will be used for the forward projection-guided interpolation at step 98.

According to one embodiment, step 98 may calculate a distance metric between the forward projected value for a dexel to be replaced, $d_{i,j,k}^{F}$, and all of the voxels along the "periphery" of the replacement region. The periphery of the replacement region is a neighborhood defined about that replacement region. For example, one embodiment may include all dexels adjacent to metal dexels in the periphery, where adjacency is defined as two dexels whose row and channel indices are within one row and/or channel of each another. The previously completed value at dexel (i,j,k−1) may also be considered a non-metal dexel and included in the periphery. The peripheral dexels may then be sorted by their distance metric to dexel (i,j,k) and some subset of the lowest distance peripheral dexels may then be chosen to define the direction along which interpolation will occur. The set of dexel indices defining the periphery of the replacement region may be defined as P and the set of voxels among which the interpolation will occur may be defined as $$\{d_{i'_n,j'_n,k'_n}^{F}\}_{n=1}^{N},$$

(i', j',k')∈P. Rather than using the values $$\{d_{i'_n,j'_n,k'_n}^F\}_{n=1}^N$$

directly, the real projection data with the same indices is used during the interpolation.

Technique 82 applies a weighted forward projection guided interpolation at step 100 to generate a completion patch. In one embodiment, the forward projection guided interpolation takes the form:

$$d_{i,j,k}^{new} = \alpha_{i,j,k} d_{i,j,k}^F + \sum_{n=1}^N \beta_n \hat{d}_{i'_n,j'_n,k'_n},\qquad \text{(Eqn. 15)}$$

where $\alpha_{i,j,k}$ may be chosen to define the influence of the estimated value on the final value and the $\beta_n$ weights may be chosen based on the calculated distance metrics. The $\beta_n$ weights may additionally depend on the dexel indices (i,j,k) so that the weighted interpolation coefficients may be normalized such that $$\alpha_{i,j,k} + \sum_{n=1}^N \beta_n = 1.$$

The $\alpha_{i,j,k}$ may be adjusted on a dexel-by-dexel basis based on the expected accuracy of the forward projected value at dexel index (i,j,k). For example, the difference between $d_{i,j,k}^F$ and the corresponding completion value calculated may be computed by applying step 72 of technique 60 (FIG. 5) and setting $\alpha_{i,j,k}$ as a function of this difference. In this fashion, the contribution of $d_{i,j,k}^F$ may be decreased by decreasing $\alpha_{i,j,k}$ as the difference increases by assuming that the forward projected value k may not be accurate due to corruption in the image domain.

Referring back to FIG. 6, after calculating the completion patch at step 100, technique 82 optionally smoothes the completion patch at step 102 (shown in phantom), similar to the smoothing described with respect to step 74 of technique 60 (FIG. 5).

Technique 82 of FIG. 6 reconstructs the now-completed projection data at step 104 to generate a metal artifact reduced CT image volume in accordance with parameter set "B," similar to step 76 of technique 60 (FIG. 5). At step 106 of FIG. 6, technique 82 re-samples the metal mask from parameter set "A" to parameter set "B," similar to step 78 of technique 60 (FIG. 5). As shown in FIG. 6, at step 108, technique 82 applies metal replacement in the newly reconstructed CT image volume in a similar fashion as step 80 of technique 60.

Figure 7:
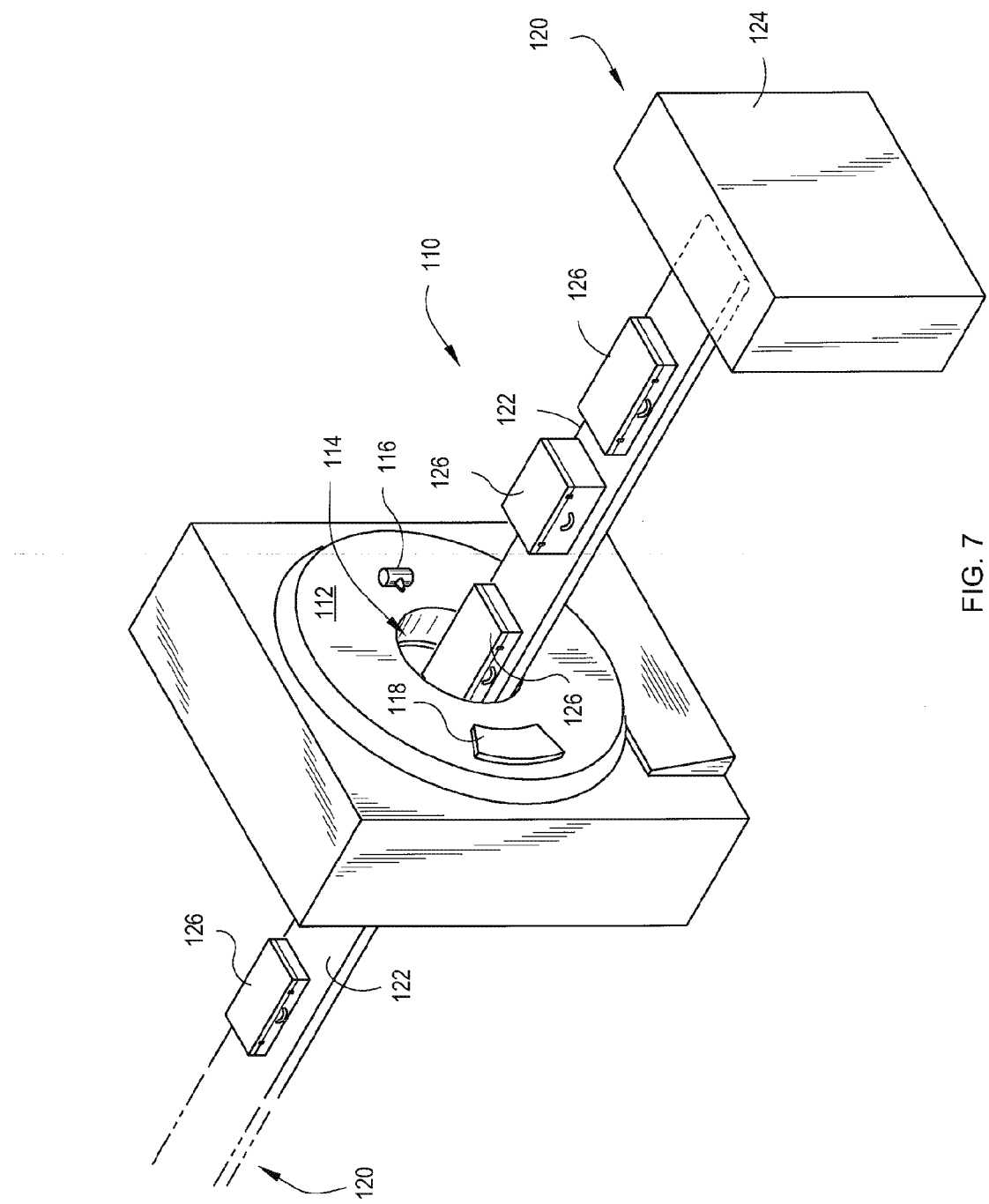
FIG. 7 is a pictorial view of a CT system for use with a non-invasive package inspection system according to an embodiment of the invention.

Referring now to FIG. 7, package/baggage inspection system 110 includes a rotatable gantry 112 having an opening 114 therein through which packages or pieces of baggage may pass. The rotatable gantry 112 houses a high frequency electromagnetic energy source 116 as well as a detector assembly 118 having scintillator arrays comprised of scintillator cells similar to that shown in FIG. 3 or 4. A conveyor system 120 is also provided and includes a conveyor belt 122 supported by structure 124 to automatically and continuously pass packages or baggage pieces 126 through opening 114 to be scanned. Objects 126 are fed through opening 114 by conveyor belt 122, imaging data is then acquired, and the conveyor belt 122 removes the packages 126 from opening 114 in a controlled and continuous manner. As a result, postal inspectors, baggage handlers, and other security personnel may non-invasively inspect the contents of packages 126 for explosives, knives, guns, contraband, etc.

Embodiments of the invention have been described with respect to single and dual energy CT imaging. However, one skilled in the art will recognize that embodiments of the invention are equally applicable to triple energy CT imaging procedures, for example. Embodiments of the invention are also equally applicable to projection-based BMD and image-based BMD. Further, embodiments of the invention have been described with respect to integrating detectors. However, one skilled in the art will recognize that embodiments of the invention may similarly be used for system employing photon counting detectors. Further, embodiments of the invention described herein are equally applicable to other types of tomographic imaging such as CT attenuation correction images for single photon emission computed tomography (SPECT) or positron emission tomography (PET), three-dimensional x-ray imaging, vascular and surgical C-arm systems, radiation therapy planning scanners, other tomographic x-ray systems, and the like.

A technical contribution for the disclosed method and apparatus is that it provides for a computer implemented method and apparatus for reduction of metal artifacts in CT images.

Therefore, in accordance with one embodiment, a computer readable storage medium has stored thereon a computer program comprising instructions, which, when executed by a computer, cause the computer to acquire a first view dataset based on x-rays received by a detector corresponding to a first energy level, reconstruct an initial image using the first view dataset, the initial image comprising a plurality of metal voxels at respective metal voxel locations, and generate a metal mask corresponding to the plurality of metal voxels within the initial image. The instructions also cause the computer to forward project the metal mask onto the first view dataset to identify metal dexels in the first view dataset, perform a weighted interpolation based on the identified metal dexels to generate a completed first view dataset, reconstruct a first final image using the completed first view dataset, the first final image comprising a plurality of image voxels corresponding to the metal voxel locations, and replace a portion of the plurality of image voxels corresponding to the metal voxel locations with smoothed metal values.

In accordance with another embodiment, a method includes reconstructing an image using an imaging dataset based on x-rays received by a detector corresponding to a first energy level, generating a metal mask from the image corresponding to metal voxel locations within the imaging dataset, and forward projecting the metal mask onto the imaging dataset. The method also includes identifying a plurality of metal dexels and a plurality of non-metal dexels within the imaging dataset based on the metal mask, removing the plurality of metal dexels from the imaging dataset, and generating a plurality of interpolated dexels via a weighted interpolation algorithm. The method further includes replacing each of the plurality of metal dexels in the imaging dataset with a respective interpolated dexel of the plurality of interpolated dexels, reconstructing a final image using the plurality of non-metal dexels and the plurality of interpolated dexels, and smoothing image voxels in the final image corresponding to the metal voxel locations.

In accordance with yet another embodiment, an imaging system includes a rotatable gantry having an opening for receiving an object to be scanned, and an x-ray source coupled to the gantry and configured to project x-rays through the opening. The imaging system also includes a generator configured to energize the x-ray source to a first energy level to generate x-rays corresponding to the first energy level, a detector having pixels therein, the detector attached to the gantry and positioned to receive x-rays projected from the x-ray source, and a computer. The computer is programmed to access a first projection dataset corresponding to the first energy level, reconstruct a first image from the first projection dataset, and segment the first image to identify metal locations. The computer is also programmed to forward project the segmentation onto the first projection dataset to identify a plurality of metal detector pixels in the first projection dataset, remove the plurality of metal detector pixels from the first projection dataset, and use a weighted interpolation to replace the removed plurality of metal detector pixels and to complete the first projection dataset. Further, the computer is programmed to reconstruct a completed first image using the completed first projection dataset and smooth portions of the completed first image corresponding to the metal locations of the first energy image.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:

1. A non-transitory computer readable storage medium having stored thereon a computer program comprising instructions, which, when executed by a computer, cause the computer to:
acquire a first view dataset based on x-rays received by a detector corresponding to a first energy level;
reconstruct an initial image using the first view dataset, the initial image comprising a plurality of metal voxels at respective metal voxel locations;
generate a metal mask corresponding to the plurality of metal voxels within the initial image;
forward project the metal mask onto the first view dataset to identify metal dexels in the first view dataset;
perform a weighted interpolation based on the identified metal dexels to generate a completed first view dataset, wherein the weighted interpolation uses historical completed data;
reconstruct a first final image using the completed first view dataset, the first final image comprising a plurality of image voxels corresponding to the metal voxel locations; and
replace a portion of the plurality of image voxels corresponding to the metal voxel locations with smoothed metal values.

2. The computer readable storage medium of claim 1 wherein the instructions cause the computer to generate the metal mask by applying a metal threshold to the initial image.

3. The computer readable storage medium of claim 2 wherein the instructions further cause the computer to perform dilation and erosion operations on the metal mask.

4. The computer readable storage medium of claim 1 wherein the instructions further cause the computer to replace the plurality of metal voxels in the reconstructed initial image with at least one of a constant value and interpolated values corresponding to nearby non-metal voxels.

5. The computer readable storage medium of claim 1 wherein the instructions further cause the computer to apply a full forward projection to the reconstructed initial image.

6. The computer readable storage medium of claim 1 wherein the instructions further cause the computer to apply a forward projection-guided interpolation to generate a completion patch corresponding to the metal dexel locations.

7. The computer readable storage medium of claim 1 wherein the instructions further cause the computer to forward project the metal mask onto the first view dataset based on a spread of a respective metal voxel onto the detector.

8. The computer readable storage medium of claim 1 wherein the instructions cause the computer to perform a weighted three-dimensional interpolation using row, channel, and view data in a neighborhood of respective metal dexels of the first view dataset being interpolated.

9. The computer readable storage medium of claim 1 wherein the instructions that cause the computer to acquire a first view dataset cause the computer to acquire the first view dataset in an axial scanning mode; and
wherein the instructions that cause the computer to reconstruct an initial image cause the computer to:
reconstruct a first plurality of image slices corresponding to a primary reconstruction volume for an axial scan; and
reconstruct a second plurality of image slices corresponding to a non-primary reconstruction volume in a direction orthogonal to an axial scan plane of the first view dataset, the non-primary reconstruction volume outside the primary reconstruction volume.

10. The computer readable storage medium of claim 1 wherein the instructions further cause the computer to:
acquire a second view dataset based on x-rays received by the detector corresponding to a second energy level;
forward project the metal mask onto the second view dataset to identify metal dexels in the second view dataset;
perform the weighted interpolation based on the metal dexels identified in the second view dataset to generate a completed second view dataset; and
reconstruct a second final image, the second final image comprising a plurality of image voxels corresponding to the metal voxel locations.

11. The computer readable storage medium of claim 10 wherein the instructions that cause the computer to perform the weighted interpolation to generate the completed first view dataset and the completed second view dataset cause the computer to:
determine a set of weighting values; and
apply the set of weighting values to corresponding metal dexels in the first and second view datasets.

12. The computer readable storage medium of claim 10 wherein the instructions that cause the computer to reconstruct an initial image cause the computer to reconstruct one of a monoenergetic image and a material decomposed image using the first view dataset and the second view dataset.

13. The computer readable storage medium of claim 10 wherein the instructions that cause the computer to reconstruct a second final image cause the computer to reconstruct one of a monoenergetic image and a material decomposed image.

14. The computer readable storage medium of claim 10 wherein the instructions cause the computer to reconstruct a second final image using the completed second view dataset.

15. The computer readable storage medium of claim 10 wherein the instructions cause the computer to:
  modify the plurality of image voxels corresponding to the metal voxel locations of the first final image to have values corresponding to expected metal values for the first energy level;
  modify the plurality of image voxels corresponding to the metal voxel locations of the second final image to have values corresponding to expected metal values for the second energy level; and
  apply a smoothing procedure on the modified plurality of image voxels.

16. The computer readable storage medium of claim 10 wherein the instructions further cause the computer to:
  modify the plurality of image voxels corresponding to the metal voxel locations of the first final image according to a weighted least squares fit;
  modify the plurality of image voxels corresponding to the metal voxel locations of the second final image according to the weighted least squares fit;
  scale the modified plurality of image voxels of the first and second final images to match one of the metal threshold and an expected value; and
  apply a smoothing procedure on the modified plurality of image voxels.

17. The computer readable storage medium of claim 16 wherein the instructions further cause the computer to combine the first final image and the second final image to generate a monoenergetic image.

18. A method comprising:
  reconstructing an image using an imaging dataset based on x-rays received by a detector corresponding to a first energy level;
  generating a metal mask from the image corresponding to metal voxel locations within the imaging dataset;
  forward projecting the metal mask onto the imaging dataset;
  identifying a plurality of metal dexels and a plurality of non-metal dexels within the imaging dataset based on the metal mask;
  removing the plurality of metal dexels from the imaging dataset;
  generating a plurality of interpolated dexels via a weighted interpolation algorithm, wherein generating the plurality of interpolated dexels uses row, channel, and view data corresponding to at least one of historical completed data and neighboring non-metal dexels;
  replacing each of the plurality of metal dexels in the imaging dataset with a respective interpolated dexel of the plurality of interpolated dexels;
  reconstructing a final image using the plurality of non-metal dexels and the plurality of interpolated dexels; and
  smoothing image voxels in the final image corresponding to the metal voxel locations.

19. The method of claim 18 wherein generating the plurality of interpolated dexels comprises generating the plurality of interpolated dexels using row, channel, and view data in a neighborhood of respective metal dexels of the imaging dataset.

20. The method of claim 18 further comprising:
  forward projecting the metal mask onto a second imaging dataset corresponding to a second energy level different from the first energy level;
  identifying a second plurality of metal dexels and a second plurality of non-metal dexels within the second imaging dataset based on the metal mask;
  removing the second plurality of metal dexels from the second imaging dataset;
  generating a second plurality of interpolated dexels via the weighted interpolation algorithm;
  replacing each of the second plurality of metal dexels in the second imaging dataset with a respective interpolated dexel of the second plurality of interpolated dexels;
  reconstructing a second final image; and
  smoothing image voxels in the second final image corresponding to the metal voxel locations.

21. The method of claim 20 further comprising:
  modifying the plurality of image voxels corresponding to the metal voxel locations of the final image to have values corresponding to expected metal values for the first energy level; and
  modifying the plurality of image voxels corresponding to the metal voxel locations of the second final image to have values corresponding to expected metal values for the second energy level.

22. The method of claim 18 further comprising smoothing the plurality of interpolated dexels using at least one neighboring dexel.

23. The method of claim 18 further comprising synthesizing a plurality of replacement voxels corresponding to the metal voxels prior to forward projecting the metal mask onto the imaging dataset, wherein the plurality of replacement voxels correspond to one of a constant value and interpolated values corresponding to nearby non-metal voxels.

24. An imaging system comprising:
  a rotatable gantry having an opening for receiving an object to be scanned;
  an x-ray source coupled to the gantry and configured to project x-rays through the opening;
  a generator configured to energize the x-ray source to a first energy level to generate x-rays corresponding to the first energy level;
  a detector having pixels therein, the detector attached to the gantry and positioned to receive x-rays projected from the x-ray source; and
  a computer programmed to:
    access a first projection dataset corresponding to the first energy level;
    reconstruct a first image from the first projection dataset;
    segment the first image to identify metal locations;
    forward project the segmentation onto the first projection dataset to identify a plurality of metal detector pixels in the first projection dataset;
    remove the plurality of metal detector pixels from the first projection dataset;
    use a weighted interpolation to replace the removed plurality of metal detector pixels and to complete the first projection dataset;
    reconstruct a completed first image using the completed first projection dataset;
    smooth portions of the completed first image corresponding to the metal locations of the first energy image;
    access a second projection dataset corresponding to a second energy level;
    forward project the segmentation onto the second projection dataset to identify a plurality of metal detector pixels in the second projection dataset;
    remove the plurality of metal dexels from the second projection dataset;
    use a weighted interpolation to replace the removed plurality of metal detector pixels and to complete the second projection dataset;

reconstruct a completed second image using the completed second projection dataset; and smooth portions of the completed second image corresponding to metal locations of the second projection dataset.

25. The imaging system of claim 24 wherein the computer is further programmed to:

modify portions of the completed first image corresponding to metal locations such that the completed first image depicts expected metal values for the metal locations at the first energy level; and modify portions of the completed second image corresponding to metal locations such that the completed second image depicts expected metal values for the metal locations at the second energy level.

26. The imaging system of claim 24 wherein the computer is programmed to apply a weighted three-dimensional interpolation using at least one of historical completed data and row, channel, and view data to replace the removed plurality of metal detector pixels.

* * * * *